US012247976B2

(12) United States Patent
Warrick et al.

(10) Patent No.: US 12,247,976 B2
(45) Date of Patent: Mar. 11, 2025

(54) SAMPLE CONCENTRATION AND DETECTION SYSTEMS AND METHODS

(71) Applicant: Salus Discovery, LLC, Monona, WI (US)

(72) Inventors: Jay Warrick, Monona, WI (US); David Beebe, Monona, WI (US)

(73) Assignee: Salus Discovery, LLC, Monona, WI (US)

( * ) Notice: Subject to any disclaimer, the term of this patent is extended or adjusted under 35 U.S.C. 154(b) by 537 days.

(21) Appl. No.: 17/313,715

(22) Filed: May 6, 2021

(65) Prior Publication Data

US 2021/0349084 A1 Nov. 11, 2021

Related U.S. Application Data

(60) Provisional application No. 63/020,832, filed on May 6, 2020.

(51) Int. Cl.
*G01N 33/543* (2006.01)
(52) U.S. Cl.
CPC ............... *G01N 33/54388* (2021.08)
(58) Field of Classification Search
None
See application file for complete search history.

(56) References Cited

U.S. PATENT DOCUMENTS

| | | |
|---|---|---|
| 2010/0209296 A1 | 8/2010 | Scherkenback et al. |
| 2013/0129580 A1 | 5/2013 | Flavin et al. |
| 2017/0022550 A1 | 1/2017 | Moore et al. |
| 2018/0217140 A1 | 8/2018 | Strong et al. |
| 2019/0187142 A1 | 6/2019 | Misner et al. |
| 2019/0383807 A1* | 12/2019 | Connelly ............... G01N 33/52 |

FOREIGN PATENT DOCUMENTS

| | | | |
|---|---|---|---|
| WO | WO 2007/097917 | 8/2007 | |
| WO | WO-2008156491 A2 * | 12/2008 | .......... B01F 13/0059 |
| WO | WO 2018/222765 | 12/2018 | |
| WO | WO 2018/236998 | 12/2018 | |
| WO | WO-2019112944 A1 * | 6/2019 | .......... G01N 21/8483 |

OTHER PUBLICATIONS

Burns, ed., Immunochemical Protocols, 3rd ed., Humana Press (2005).
Harlow and Lane, Antibodies: A Laboratory Manual, Cold Spring Harbor Laboratory (1988).
Köhler et al. Continuous cultures of fused cells secreting antibody of predefined specificity. Nature, 1975; 256: 495-497.
Kozbor et al., The production of monoclonal antibodies from human lymphocytes. Immunology Today, 1983; 4(3): 72-79.
Tsai et al., Development a stacking pad design for enhancing the sensitivity of lateral flow immunoassay. Scientific Report, Nov. 23, 2018;8(1):17319.
Sharma A. et al. "Magnetic field assisted preconcentration of biomolecules for lateral flow assaying", Sensors and Actuators B: Chemical, vol. 285, Apr. 1, 2019, pp. 431-437.

* cited by examiner

*Primary Examiner* — Ann Montgomery
*Assistant Examiner* — Chau N. B. Tran
(74) *Attorney, Agent, or Firm* — Casimir Jones, S.C.; Rikki A. Hullinger (57) ABSTRACT

Provided herein are devices, systems, and methods for concentration and detection of sample components. In particular, provided herein are lateral flow devices, systems, and methods that utilize flow control of samples.

22 Claims, 9 Drawing Sheets

| | # of stripes | [Beads] | Dispense rate |
|---|---|---|---|
| A | 3 | 1x (10 mg/mL) | 1x (0.766 uL/mm) |
| B | 3 | 2x | 1x |
| C | 6 | 1x | 1x |
| D | 6 (3,3) | 1x, ½ x | 1x, 3x |
| E | 3 | ⅓ x | 3x |
| F | 6 | ⅓ x | 3x |

SAMPLE CONCENTRATION AND DETECTION SYSTEMS AND METHODS

This application claims priority to provisional application no. 63/020,832, filed May 6, 2020, which is herein incorporated by reference in its entirety.

FIELD

Provided herein are devices, systems, and methods for concentration and detection of sample components. In particular, provided herein are lateral flow devices, systems, and methods that utilize flow control of samples.

BACKGROUND

There is a great need for cost-effective, easy to use systems, methods, and devices for analyzing biological samples. Many commercially available systems cost tens to hundreds of thousands of dollars and have many moving parts which make them prone to failure. Because of the cost and complexity of such systems, their use has generally been limited to clinical laboratories that have the personnel and services needed to support their operation and maintenance.

One class of fully integrated automated analyzers, represented by the Abbott ARCHITECT, Siemens CENTAUR, Roche ELECSYS, and others, perform immunoassays. Another class of modular analyzers, represented by the Abbott m2000, Roche COBAS, bioMérieux NUCLISENS, Cepheid GENEXPERT System analyzers and others, perform nucleic acid assays. Much of the complexity of these systems is a result of separation steps involved in processing the assays.

Modular systems are also frequently used in research laboratories. Immunoassay separations may be performed by plate washers such as Titertek MAP-C2, BioTek ELx50, Tecan PW 96/384 and others. Nucleic acid separations are performed by systems such as the Applied Biosystems PRISM 6100, Invitrogen IPREP, Thermo Scientific KINGFISHER, Promega MAXWELL systems, and others.

Existing assay systems and methods are complex, expensive and not suitable for use in many settings, especially in the developing world. Additional systems and methods are needed.

SUMMARY

Provided herein are devices, systems, and methods for concentration and detection of sample components. In particular, provided herein are lateral flow devices, systems, and methods that utilize flow control of samples.

For example, in some embodiments, provided herein is a sample concentration device, comprising: a substrate comprising a plurality of wicking regions and plurality (e.g., 1, 2, 3, 4, 5, 6, or more) of capture regions (e.g., arranged in a parallel orientation), wherein each of the capture regions comprises a plurality of analyte specific capture reagents, and optionally, wherein each of the capture regions comprises a plurality (e.g., two) fluid isolation zones on either side of each capture region, wherein the fluid isolation zones are oriented at an angle (e.g., perpendicular angle) to a direction of capture flow. In some embodiments, the fluid isolation zones comprise a compressed or cut region of the substrate (e.g., in some embodiments, the wicking regions and the capture regions are physically separate components). In some embodiments, the substrate comprises a porous material. In some embodiments, the capture regions have a width approximately equal to the depth of the substrate (e.g., with a ratio of width to depth of 1:3 to 3:1). In some embodiments, the capture regions are spaced at a width of approximately 1.3 times (e.g., 0.8, 0.9, 1.0, 1.1, 1.2, 1.3, 1.4, 1.5, etc.) the depth of the substrate. In some embodiments, the analyte specific capture reagent comprises particles comprising an analyte specific binding molecule (e.g., an antibody, a lectin, a carbohydrate, a dye, biotin, or streptavidin). In some embodiments, two or more different analyte binding molecules specific for two or more different analytes are provided. In some embodiments, the particles are movable in a magnetic field. In some embodiments, the device further comprises an input wick in fluid communication with said sample capture regions. In some embodiments, the sample capture regions are 0.1-15 mm long, 0.1-15 mm wide and 0.025-5 mm thick (e.g., each dimension plus or minus 1%, 5%, 10%, 15%, or 20%). In some embodiments, the analyte-specific capture reagents are applied via spraying.

Further embodiments provide a system, comprising: a) a sample concentration device as described herein; and b) a lateral flow assay device. In some embodiments, the sample concentration device is in operable communication with the lateral flow assay device (e.g., an input component (e.g., pad) of the lateral flow assay device).

In some embodiments, the system further comprises an elution component in operable communication with the sample concentration device. In some embodiments, the elution component is a porous substrate (e.g., cellulose fiber, cotton fiber, or glass/cotton fiber). In some embodiments, the elution component is located downstream of the sample concentration device and the lateral flow assay device is located upstream of the sample concentration device. In some embodiments, the elution pad comprises dehydrated elution buffer.

In some embodiments, the system further comprises a siphon component (e.g., to siphon away fluid lacking analyte and thus reduce dead volume). For example, in some embodiments, the input pad is in operable communication with a siphon pad comprising a plurality of siphon arms oriented at an angle from (e.g., perpendicular to) the input pad. In some embodiments, the siphon pad comprises a porous substrate. In some embodiments, the siphon pad is configured to hold up to 100 μl (e.g., up to 20, 30, 40, 50, 60, 70, 80, 90, or 100 μl) of fluid.

In some embodiments, the siphon component directs flow in a direction independent from the flow path (e.g., horizontal or vertical, although other directions are specifically contemplated). In some embodiments, the siphon component is integrated into a LFA test strip.

In some embodiments, the system further comprises a fluid (e.g., elution buffer, wash buffer, pre-treatment solution (e.g., 10% bovine serum albumin in phosphate buffered saline) and/or a sample).

In some embodiments, the system comprises a LFA comprising a sample detection membrane comprising an upstream zone, a test region (e.g., line or spot) zone, and a control zone, wherein the test region zone has a width at least 25% (e.g., at least 25%, 35%, 45%, 50%, 55%, 60%, or 70%) less that the upstream zone and the downstream zone.

Additional embodiments provide a method of concentrating an analyte, comprising: contacting a sample comprising the analyte with a sample concentration device as described herein such that the analyte binds to the capture regions. In some embodiments, the method further comprises the step of eluting the analyte from the capture regions. In some embodiments, the analyte is eluted in a direction angled away from (e.g., perpendicular to) the direction of the fluid flow used in the contacting step.

Yet other embodiments provide a method of concentrating and detecting an analyte, comprising: a) contacting a sample comprising an analyte with a system as described herein; and b) concentrating the analyte using the system. In some embodiments, the method further comprises detecting the analyte.

Certain embodiments provide a lateral flow device, comprising: a) a lateral flow membrane comprising a plurality of capture regions comprising a plurality of analyte specific binding molecules; b) a plurality of wicking pads and an absorbent pad; and c) a conjugate pad comprising a plurality of detection moieties (e.g., nanoparticles) conjugated to a plurality of analyte specific binding molecules. In some embodiments, the wicking pads comprise an input wick and an output wick. In some embodiments, the device comprises a first configuration where the input wick and the output wick are in operable communication with the lateral flow membrane; and a second configuration where the conjugate pad and the absorbent pad are in operable communication with the lateral flow membrane. In some embodiments, analyte specific binding molecules are immobilized to said capture region using protein G.

Also provided herein is a method of concentrating and detecting an analyte, comprising: a) contacting a sample comprising an analyte with the device described above in a first configuration such that analyte in the sample is bound by the analyte-specific binding molecules; b) subsequently reconfiguring the device to the second configuration; and c) detecting the analyte using the device in the second configuration.

Further provided is a method of concentrating and detecting an analyte, comprising: a) contacting a sample comprising the analyte with a lateral flow device, comprising: i) a lateral flow membrane comprising a plurality of capture regions comprising a plurality of analyte specific binding molecules; and ii) a plurality of wicking pads and an absorbent pad; b) placing a conjugate pad comprising a plurality of detection moieties conjugated to a plurality of analyte specific binding molecules in fluid communication with the lateral flow device such that the particles flow onto the lateral flow device and bind to the analyte bound to the analyte specific binding molecules in the capture region; and c) detecting the analyte.

In some embodiments, provided is a lateral flow assay device, comprising: a sample detection membrane comprising an upstream zone, a test region zone, and a control zone, wherein the test region zone has a width at least 25% (e.g., at least 25%, 35%, 45%, 50%, 55%, 60%, or 70%) less that the upstream zone and the downstream zone. In some embodiments, the test region (e.g., line) zone has a length at least 1× (e.g., at least 1.5, 2.0, 2.5, or 3.0) times as wide as the test line. In some embodiments, the test region of a detected sample is at least 20% (e.g., at least 20%, 25%, 30%, 35%, or 40%) more intense than a device with a test zone of the same width as the upstream and downstream zones. In some embodiments, the device further comprises one or more of a conjugate pad, a sample concentration component, an input wick, and an output wick.

Yet other embodiments provide a method of capturing and/or concentrating an analyte, comprising: a) contacting a sample comprising an analyte with a substrate-based capture and concentration device configured to capture analyte in a capture region, wherein the length of the capture region is approximately equal to the length of the capture region and comprising a plurality of elements configured to utilize plug-flow of fluid through the capture regions, and wherein the contacting is performed under minimum flow velocity; and b) eluting the analyte from the capture region at an angle (e.g., perpendicular or other angle), or in line to the angle of contacting. In some embodiments, the concentration of said analyte after eluting is described by $$C_T = \frac{C_T}{C_{T,i}} = \frac{1 - \tanh(\frac{x \cdot a}{2})}{2}, \quad (1)$$

wherein $$\alpha = \frac{C_{T,i} k_{on}}{v_{flow}} \left( \frac{C_{L,tot}}{K + C_{T,i}} + 1 \right), \quad (2)$$

wherein $C_{T,i}$ is the concentration of the analyte in the sample; K is the dissociation constant of the analyte specific capture reagent and is equal to the ratio of the off-rate and on rate of the interaction, $k_{off}/k_{on}$; $C_{L,tot}$ is the total concentration the analyte specific capture reagent in the capture region; and $v_{flow}$ is the velocity of the sample through the device. In some embodiments, the device minimizes dead volume.

In some embodiments, the analyte is, for example, a protein, a peptide, a carbohydrate, a lipid, a nucleic acid, a hormone, a metabolite, or a microorganism specific marker. In some embodiments, the sample is, for example, a blood sample, a blood product sample (e.g., serum, plasma), a urine sample, a food sample, sputum, mucus, stool, water, semen, milk, or a saliva sample. In some embodiments, the sample is obtained from a collection component (e.g., nasal or throat swab). In some embodiments, the sample is suspended or dissolved in a buffer.

Additional embodiments are described herein.

BRIEF DESCRIPTION OF THE DRAWINGS

FIG. 5 shows different methods to enhance capture and elution. (A) The cross-sectional area of the capture region (brown) normal to the direction of capture flow is enlarged to minimize flow velocity while maximizing volumetric flow rate. (B) Although elution can be performed in the direction of concentration (x-direction), perpendicular to the plane of the pad (z-direction), another option is to elute in the y-direction, or directions in between. The flow front of fluid passing through porous media approximates plug flow (e.g., remains flat and normal to the direction of flow). (C) Only the flow front with accumulated analyte need be removed from the capture region instead of the entire volume of the capture region. (D) The capture zone (shaded)

and the input and output regions are separated by cutting to eliminate dead volume contribution from the input and output regions prior to eluting from the capture zone. Elution can then be performed in any direction (x, y, z, or directions in between). (E) The capture zone (shaded) and the input and output regions start as 3 separate components that are initially in contact, then separated after concentration. Elution can then be performed in any direction (x, y, z, or directions in between).

DEFINITIONS

To facilitate an understanding of the present disclosure, a number of terms and phrases are defined below:

The term "sample" is used in its broadest sense. On the one hand it is meant to include a specimen or culture. On the other hand, it is meant to include both biological and environmental samples. A sample may include a specimen of synthetic origin. Biological samples may be obtained from animals (including humans) and encompass fluids (e.g., urine, blood, blood products, sputum, saliva, etc.), solids, tissues, and gases. Biological samples include blood products, such as plasma, serum and the like. In some embodiments, samples contain or are suspected of containing a microorganism (e.g., a pathogenic or disease-causing microorganism).

"Analyte," as used herein, is the substance to be detected which may be present in the test sample, including, biological molecules of interest, small molecules, pathogens, and the like. The analyte can include a cell, a microorganism, a protein, a polypeptide, an amino acid, a nucleotide target and the like. The analyte can be soluble in a body fluid such as blood, blood plasma or serum, urine or the like. The analyte can be in a tissue, either on a cell surface or within a cell. The analyte can be on or in a cell dispersed in a body fluid such as blood, urine, breast aspirate, or obtained as a biopsy sample.

A "capture reagent," as used herein, refers to a labeled or unlabeled specific binding member, which is specific either for the analyte as in a sandwich assay, for the indicator reagent or analyte as in a competitive assay, or for an ancillary specific binding member, which itself is specific for the analyte, as in an indirect assay. The capture reagent can be directly or indirectly bound to a solid phase material before the performance of the assay or during the performance of the assay, thereby enabling the separation of immobilized complexes from the test sample.

The "indicator reagent" comprises a "signal-generating compound" ("label") that is capable of generating and generates a measurable signal detectable by external means. In some embodiments, the indicator reagent is conjugated ("attached") (e.g., covalently or non-covalently) to a specific binding member. The indicator reagent can be a member of any specific binding pair, including either hapten-anti-hapten systems such as biotin or anti-biotin, avidin or biotin, a carbohydrate or a lectin, a complementary nucleotide sequence, an effector or a receptor molecule, an enzyme cofactor and an enzyme, an enzyme inhibitor or an enzyme and the like. An immunoreactive specific binding member can be an antibody, an antigen, or an antibody/antigen complex that is capable of binding either to the polypeptide of interest as in a sandwich assay, to the capture reagent as in a competitive assay, or to the ancillary specific binding member as in an indirect assay. When describing probes and probe assays, the term "reporter molecule" may be used. A reporter molecule comprises a signal generating compound as described hereinabove conjugated to a specific binding member of a specific binding pair, such as carbazole or adamantane.

The various "signal-generating compounds" (e.g., labels) contemplated include chromagens, catalysts such as enzymes, luminescent compounds such as fluorescein and rhodamine, chemiluminescent compounds such as dioxetanes, acridiniums, phenanthridiniums and luminol, radioactive elements, nanoparticles (e.g., metal particles) and direct visual labels. Examples of enzymes include alkaline phosphatase, horseradish peroxidase, beta-galactosidase and the like. The selection of a particular label is not critical, but it should be capable of producing a signal either by itself or in conjunction with one or more additional substances.

As used herein, the term "substrate" refers to a solid or semi-solid material for use in performing sample concentration and/or detection. In some embodiments, substrates are porous. Examples of substrates include but are not limited to, membrane, films, multi-well plates, emulsions (e.g., 2-phase emulsions), lipid bilayers, micelles, and the like.

As used herein, the terms "detect", "detecting", or "detection" may describe either the general act of discovering or discerning or the specific observation of a detectably labeled composition.

The term "antibody" herein is used in the broadest sense and encompasses various antibody structures, including but not limited to monoclonal antibodies, polyclonal antibodies, multispecific antibodies (e.g. bispecific antibodies), and antibody fragments so long as they exhibit the desired antigen-binding activity. Also included are antibody fragments having an Fc region, and fusion proteins that comprise a region equivalent to the Fc region of an immunoglobulin.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$, single-chain antibody molecules (e.g. scFv), diabodies, and multispecific antibodies formed from antibody fragments.

DETAILED DESCRIPTION

Provided herein are devices, systems, and methods for concentration and detection of sample components. In particular, provided herein are lateral flow devices, systems, and methods that utilize flow control of samples.

Substrate-based sample capture and/or concentration is a technology for isolating and concentrating analytes. Although it can have many embodiments, it most often involves the use of capillary action to induce flow through a bed of capture beads. Many different variables contribute to the optimization of sample capture. Furthermore, many of these parameters are associated with both costs and benefits, leading to important optima for maximizing performance.

Figure 10:
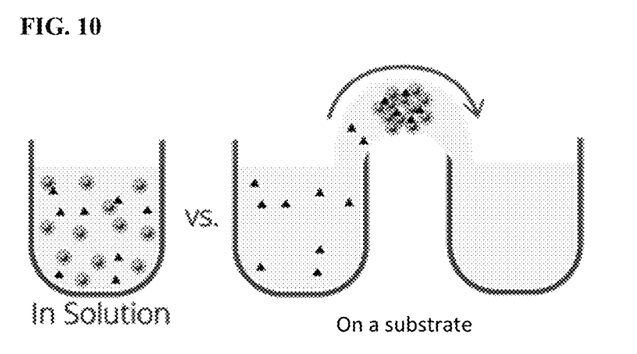
FIG. 10 shows a comparison of preconcentration via beads dispersed in solution vs. via substrate-based concentration methods of embodiments of the present disclosure. (left) Capture in solution. (right) Substrate-based concentration.

Concentration steps using a substrate (See e.g., WO 2018/236998; herein incorporated by reference in its entirety) performed prior to lateral flow assays can provide a 100-10,000 fold improvement in the fold concentration of an analyte from solution compared to traditional pre-concentration of analyte using beads in solution. This gain is provided by two fundamental changes (FIG. 10). Using the same number of capture molecules, capture via substrate-based sample concentration increases the concentration of the capture molecule by 100-1000 fold compared to being dispersed in solution. This drives the kinetics of binding to promote capture of analytes at low concentration by a corresponding fold increase. Secondly, as analyte passes through the capture region in a directional fashion, analyte is gradually depleted as it flows. With a sufficiently long capture region, capture asymptotically approaches 100%. In solution, capture is limited by equilibrium. The primary tradeoff for capture prior to lateral flow is time. In such steps, the sample is typically allowed to pass through the capture region at a velocity dictated by the flow, capture region geometry, and the binding kinetics. In solution, equilibrium with the entire solution occurs rapidly. When analyte concentrations are high relative to the dissociation constant of the capture method, capture in solution can perform nearly equivalently to substrate capture and do so very quickly. However, when analyte concentrations are low relative to the dissociation constant of the capture method, substrate-based concentration dramatically outperforms capture in solution.

Accordingly, provided herein are systems, devices, compositions and methods for substrate-based sample capture and concentration (e.g., for use with lateral flow assays). A key measure of overall performance is the fold-concentration that can be achieved when isolating analytes. Assuming a perfect system, the maximum possible fold-concentration, $FC_{max}$, that can be achieved is simply the volume of the original sample that can be processed or allowed to flow through the capture region of the device, $Vol_{sample}$, divided by the volume in which the captured analyte is eluted, $Vol_{elution}$ (Eq 1).

$$FC_{max} = \frac{Vol_{sample}}{Vol_{elution}} \quad [1]$$

A representation of performance that includes inefficiencies associated with capture, elution, and transfer of the eluted material into a downstream assay is described by Eq 2.

$$FC = \frac{Vol_{sample}}{Vol_{elution}} \times \text{Capture } Eff. \times \text{Elution } Eff. \times \text{Transfer } Eff. \quad [2]$$

Eq 2 is used term-by-term as a basis to guide description of exemplary embodiments of the disclosure that optimize performance in capture efficiency, $Vol_{sample}$, $Vol_{elution}$, transfer efficiency, and elution efficiency, each of which is described in detail below.

There are challenges in trying to optimize performance. Changing one feature of a system to provide one benefit (e.g., shorter assay time) can adversely impact other performance characteristics (e.g., lower signal, lower sensitivity, lower specificity, etc.). Because system design involves many different features, each of which can independently or cooperatively improve or adversely impact other features when altered, there are many design challenges to achieve a balanced, optimal result. Depending on the desired performance of a particular system, different optimizations may be needed.

Capture Efficiency

To better understand the parameters that influence capture efficiency, a mathematical model of substrate-based capture was built. This model is a steady-state or quasi-steady state solution to analyte capture from a fluid passing through a porous media where the capture moiety is immobilized in/on the media. Although the kinetics of capture for this model are defined by a Ricatti form differential equation, an appropriate solution could not be found in the literature or via symbolic math softwares (Mathematica, Wolfram Alpha, and Maxima). Standard approaches to the solution resulted in use of the tangent (tan) or log functions, neither of which could be used to satisfy the boundary conditions of the problem. By investigating logarithmic and trigonometric identities and derivatives, the closely related hyperbolic tangent function (tanh) was identified as a solution that satisfied the boundary conditions of the problem.

The final solution for the (quasi)-steady-state concentration profile of the target analyte in solution, $C_T$, normalized to the incoming concentration of target, $C_{T,i}$, is provided below.

$$\tilde{C}_T = \frac{C_T}{C_{T,i}} = \frac{1 - \tanh\left(\frac{x \cdot a}{2}\right)}{2} \text{ where} \quad [1]$$

$$\alpha = \frac{C_{T,i} k_{on}}{v_{flow}} \left(\frac{C_{L,tot}}{K + C_{T,i}} + 1\right) \quad [2]$$

Upstream of flow at $x \to -\infty$, $\tilde{C}_T = 1$, while at $x \to \infty$, $\tilde{C}_T = 0$. However, ideally, the length over which the solution transition from 1 to 0 is shorter than the length of the capture region within the porous material, L. From Eq 1, one can see that the length of the concentration profile is completely dictated by a single scaling factor, $\alpha$. From this, one can define a characteristic length of the system as $\pm 2/\alpha$, resulting in an estimated profile length of $4/\alpha$. The value of a integrates the influence of many basic system parameters. This steady-state solution provides insight into the relative importance of multiple key parameters of capture based upon physical principles of conservation of mass and reaction kinetics. When using substrate-based capture to aid detection of rare analytes, a can be simplified even further to Eq 3.

$$\text{when } C_{T,i} \ll K \ll C_{L,tot}, \text{ then } \alpha \approx \frac{C_{T,i} k_{on} C_{L,tot}}{v_{flow} K} = \frac{C_{T,i} k_{on}^2 C_{L,tot}}{v_{flow} k_{off}} \quad [3]$$

In Eq 3, $C_{T,i}$ is the initial or incoming concentration of target analyte into the capture device. K is the dissociation constant of the capture moiety used to capture the ligand and is equal to the ratio of the off-rate and on rate of the interaction, $k_{off}/k_{on}$. $C_{L,tot}$ is the total concentration (i.e., both bound and unbound forms) of the capture ligand in the capture region of the device. $v_{flow}$ is the velocity of the fluid sample, which is assumed to be traveling in the positive x-direction.

In general, the length required for capture, $$\frac{4}{\alpha},$$

is less than the actual length of the capture region, L. Therefore, to assure a high percentage of the target analyte is captured before it leaves a porous material, the most important parameter is the on-rate of the capture mechanism, $k_{on}$. The squared dependence relative to other parameters of the system is not obvious. Likewise, the fraction of captured analyte increases with increasing concentration of capture ligand (e.g., antibody), $C_{L,tot}$, decreasing flow velocity, $v_{flow}$, and decreasing off-rate of captured analyte, $k_{off}$. Also, as $C_{T,i}$ decreases, capture efficiency also decreases. These influences are simultaneously considered along with other factors driving the performance of analyte capture.

Figure 1:
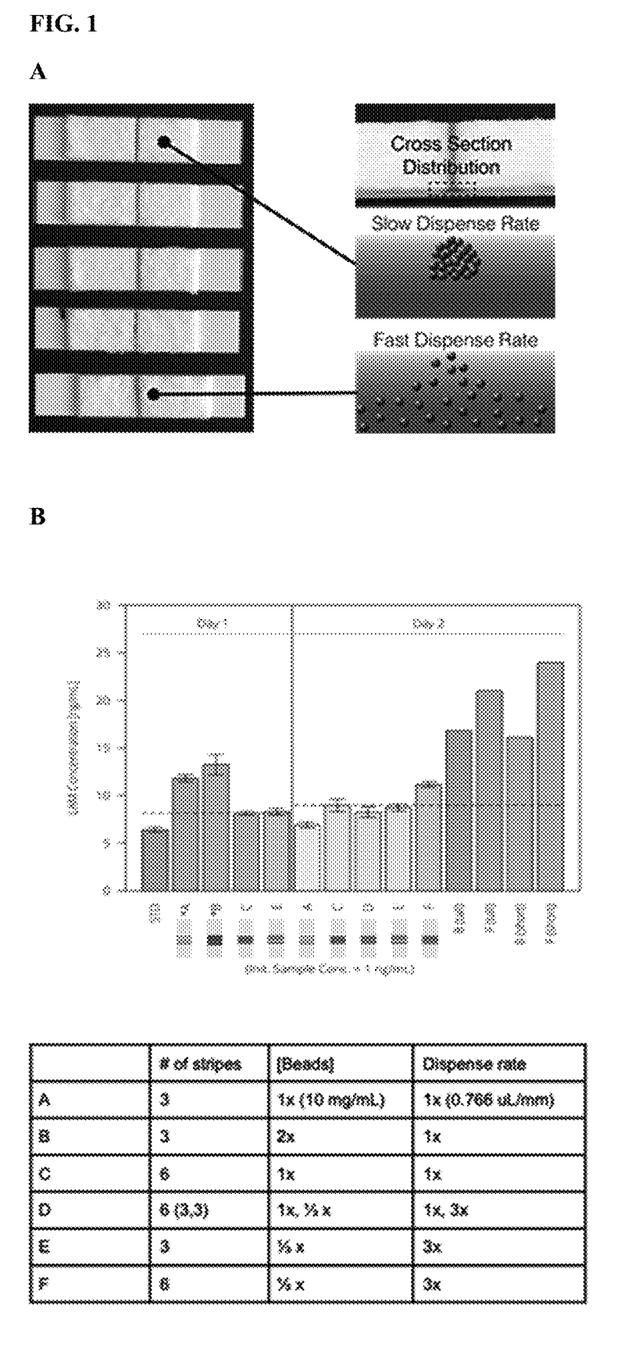
FIG. 1 shows concentration data. (A) Illustration of bead distribution pattern. (B) Pre-concentration using different bead distributions.

The distribution of capture molecule (e.g., antibodies or other binding molecules on beads or other particles) throughout the capture region impacts capture efficiency. In existing substrate-based concentration methods, magnetic beads are placed in the capture region by dispensing a slurry of functionalized beads onto the porous absorbent material that comprises the capture pad. By varying dispense rates and the velocity at which the nozzle travels during dispensation, one can generate different bead distribution patterns in the absorbent pad material (FIG. 1A). It was found that 2.3 µL/mm produces an advantageous distribution of 2.8 µm diameter beads through the 0.75 µm thick Tremont D material. Higher dispense rates (higher µL/mm) caused the slurry to be distributed too diffusely and could result in flooding of the absorbent material. Slower rates resulted in poor infiltration of the bead slurry into the absorbent material. Thus, these results illustrate the need for good, even distribution into the depth of the material without diffusing extensively in the lateral direction to cause flooding and dilution of the capture substrate. With different bead, sizes, suspension solution, material, and dispense equipment, specific parameters change. Accordingly, in some embodiments, compositions and methods of the disclosure utilize approximately a 1:1 (e.g., 1:3 to 3:1) depth to width ratio of beads or particles in the material for each capture region that is dispensed. Some beads wick laterally to make definition of the width fuzzy, but it is preferred to get 75% percent of the beads contained within a width that is equal to the material height.

It was also found that one can generate a longer capture region by creating multiple (e.g., 2, 3, 4 5, 6, or more) parallel capture regions using the above design features. In some embodiments, the capture regions are spaced to achieve as uniform a distribution of beads between capture regions as possible. In some embodiments, the capture regions are spaced ~1.3 (e.g., 0.8, 0.9, 1.0, 1.1, 1.2, 1.3, 1.4, 1.5, etc.) times the depth of the material (FIG. 1B). In the embodiment shown in FIG. 1A, the capture regions are illustrated as stripes or lines. However, other geometric configurations are specifically contemplated.

It was also found that spraying, instead of traditional fluid dispensing, can improve capture performance, allowing a wider and more uniform distribution of beads to be applied. In some embodiments, beads are prepared as a slurry and applied through a pad material. For example, in some embodiments, 2.8 µm diameter beads are prepared as a 10 mg/mL slurry and applied through the 0.75 µm thick Tremont D material at a dispense rate of 4.6 µL/mm and air pressure of 2.5 psi. As with traditional dispensing, it is possible to perform multiple applications (e.g., on top of one another or next to one another) to control bead distribution further. An advantage of spraying is that it reduces the number of steps to generate a more optimal bead distribution, which not only reduces manufacturing time but also increases reproducibility.

Vol$_{sample}$

Figure 2:
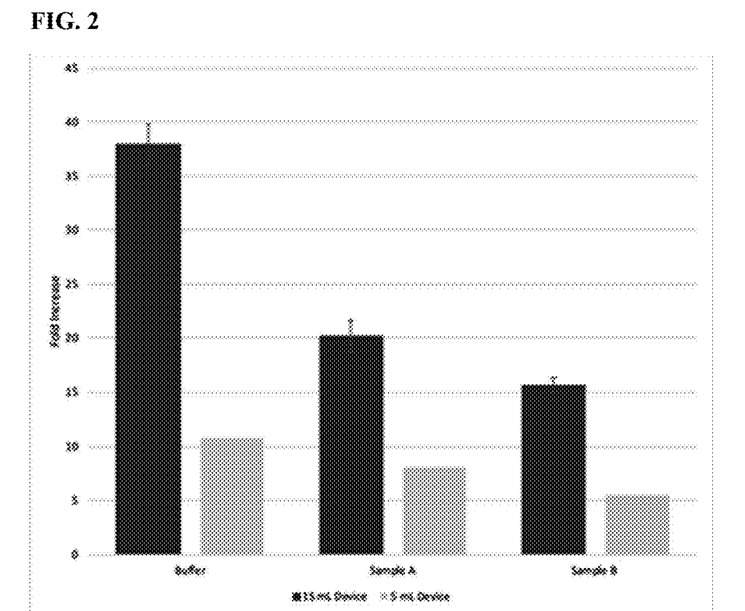
FIG. 2 shows that processing more volume increases the total amount of captured analyte which can then be eluted in the same volume, producing a higher overall fold-concentration.

The greater the volume of sample that can be processed in the amount of time allowed by an application, the greater the total amount of analyte that can be captured for eventual elution (FIG. 2). To maximize the amount of flow through the capture region, it is preferred to maximize the driving force in the system, and minimize resistance and opposing forces.

Driving force is dictated primarily by capillary wetting of materials. In some exemplary sample concentration systems, fluid first travels through an input wick, then the porous capture material, then into the output absorbent pad. To promote flow through the system, capillary force of the materials increases from input to output and is typically associated with a decrease in pore size and increase in sample-philicity (e.g., increasingly hydrophilic for aqueous samples). Furthermore, when materials wick fluid anisotropically, material is shaped and oriented such that fluid reaches the perimeter of the absorbent pad simultaneously in all directions. For example, if fluid wicks 3 times faster in the x direction compared to the y, the absorbent pad would be cut to be 3 times longer in the x direction than in the y.

Capillary force overcomes fluidic resistance and gravitational pressure heads in order to drive fluid flow. Fluidic resistance is minimized by (i) minimizing viscosity (e.g., via avoiding use of polymeric surfactants), (ii) maximizing pore size in the input wick and capture region, and (iii) minimizing lengths of materials. Gravitational pressure heads are minimized by reducing heights of fluid wicking out of the input well. In fact, it is possible to leverage gravitational pressure heads as an additional or alternative driving force to aid fluid flow.

In some embodiments, a highly porous input wick (e.g., 4 mm×10 mm×17 mm, Porex S008432), 0.75 mm×10 mm×8 mm Tremont D capture pad, and 22.5 mL of absorbent pad (Millipore CFSP223000, 19 stacked sheets 0.81 mm×19.75× 74 mm) are connected in sequence to wick 15-16 mL of sample (e.g., urine or buffer) from the input wick to the absorbent pads through the capture pad in, for example, 30-60 minutes. In some embodiments, the capture pad is fixed to a plastic backing coated with adhesive to provide support. In some embodiments, the plastic backing also provides a spring-like compliance for robustly connecting the components using the following strategy. For example, in some embodiments, the capture pad is brought into a ~1 mm interference with the input wick and absorbent pad. In this example, the highly porous wick material is much more compliant than the absorbent pad material. In such a case, the backing card is stiffly supported at the contact point with the wick, causing the wick to compress when brought into interference with the capture pad. At the contact with the absorbent pad, bending is induced in the plastic backing when brought into interference with the capture pad. Thus, the connection strategy provides compliance at both contact points for robust performance.

Figure 11:
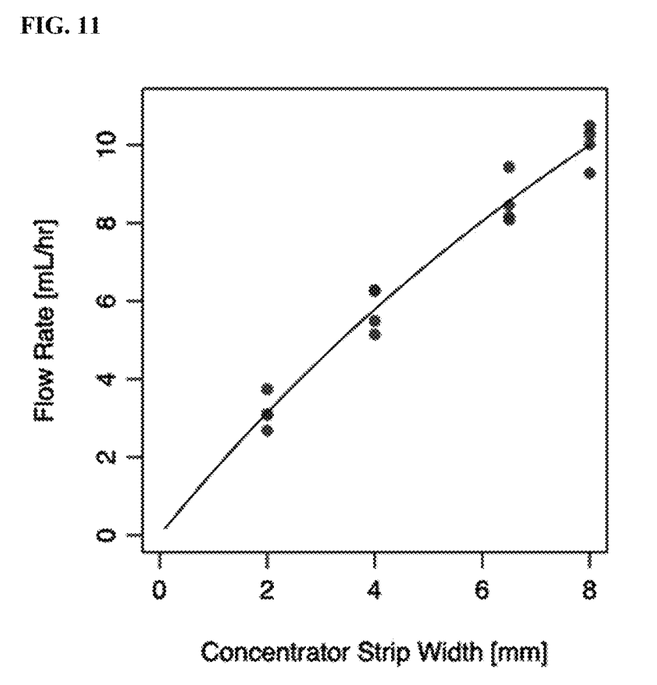
FIG. 11 shows the impact of capture pad geometry on flow rate of sample through the device during analyte capture.

In some embodiments, as illustrated in FIG. 11, the capture pad (concentrator strip) is the primary source of resistance to flow. In such a case, the width of the capture pad is used to tune flow rate without significantly altering flow velocity.

Figure 3:
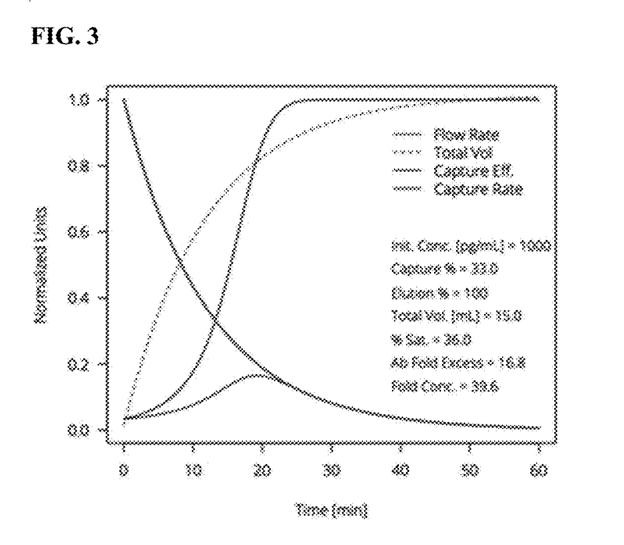
FIG. 3 shows quasi-steady state simulation of substrate-based capture using a mathematical model of embodiments of the present disclosure.

While the maximum possible fold-concentration is limited by the amount of sample that can be processed, one can see from the mathematical model (Eq 1-3) that flow velocity (as opposed to volumetric flow rate), should be minimized. Ideally, the flow velocity through the capture region is such that the product of the volumetric flow rate and capture efficiency are maximal. This occurs when the length required to capture the large majority of analyte is approximately equal to the length of the capture region, L. If fluid flows slower, less sample is processed yet capture efficiency does not improve. If fluid flows faster, more sample is processed, yet capture efficiency suffers even more, leading to an overall reduction in the rate of analyte captured. This can be seen using the mathematical model above to simulate capture when flow rate decays exponentially over time (FIG. 3).

Figure 4:
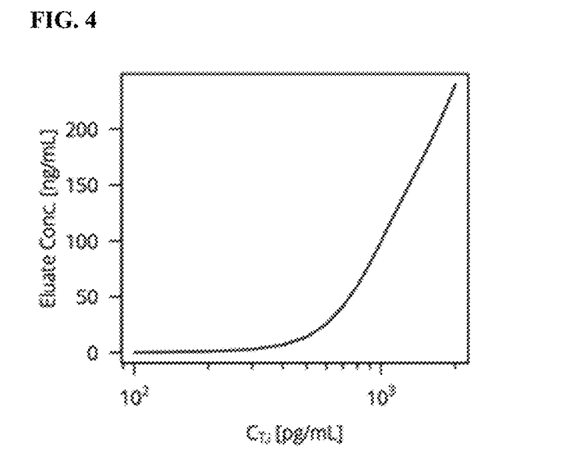
FIG. 4 shows leveraging of steady capture flow rates over time to generate a cutoff sensitivity for substrate-based concentrations of analytes.

Such a model also helps to demonstrate how the technology of embodiments of the present disclosure is specifically optimized to successfully concentrate analyte at (or above) a specific threshold concentration. When flow rate is made more constant, performance depends strongly on the incoming concentration of analyte. Performance drops steeply when the length of the capture region needed to capture low analyte concentrations becomes larger than the actual length of the capture region. This behavior is illustrated in FIG. 4 and is particularly advantageous for diagnostic assays where a threshold level of detection is important for providing a True/False or Yes/No test. At or above the threshold concentration, the assay performs near optimally to provide high sensitivity; while, below the threshold, assay performance suffers dramatically to minimize false positive results (i.e., to maximize specificity).

Given that capture efficiency is dependent upon flow velocity and not volumetric flow rate, in some embodiments, the geometry of the capture region is altered to more optimally process the sample. In some embodiments, a larger cross-section of the capture region is used to enable a higher volumetric flow rate while maintaining a constant flow velocity. The tradeoff to enlarging the cross-section of the capture region is that, for a given length of the capture region, L, the volume of the capture region grows. Therefore, more capture reagents are needed to maintain $C_{L,tot}$. Likewise, depending upon how analyte is eluted from the capture region, increasing the volume of the capture region may be associated with an increase in elution volume.

Typically, the elution volume scales with the volume of the capture region. Therefore, if the length of the capture region is made only just sufficiently long enough to ensure efficient capture for the duration of capture, then the volume of the capture region is minimized while maximizing performance. During long-term capture of analyte, substrate becomes maximally bound with analyte. As the substrate becomes maximally bound, the concentration profile of bound analyte shifts downstream. Therefore, the length of the capture region should be sufficient to encompass the length of the capture profile as well as any shift during capture. The model also provides a way to estimate the rate at which the profile shifts (Eq 4).

$$v_{profile} = \frac{v_{flow}}{1 + \frac{C_{L,tot}}{K + C_{T,i}}} \quad [4]$$

For example, when detecting lipoarabinomannan (LAM) in urine, it was found experimentally that the length and subsequent translation of the capture concentration profile is less than 6 mm when $C_{T,i} > 1$ ng/mL and the average vflow~15 mL/hr for the capture pad geometry (10 mm×8 mm×0.75 mm) and magnetic beads being tested (M270 dynabeads, 6 stripes). This is evidenced by the fact that when the 3 downstream bead stripes are quantified for LAM compared to the 3 upstream stripes, the 3 downstream stripes contain far less captured LAM than the upstream stripes and capture efficiency is ~30%. However, when $C_{T,i} << 1$ ng/mL (e.g., ~10 pg/mL), capture efficiency drops to <3% for the same configuration. Given the above considerations, the geometry of the capture region depends highly upon the available capture molecules (e.g., antibody affinity), the method of incorporation into the capture region (e.g., bead surface chemistry and bead distribution), sample size and flow rate, and initial analyte concentration in the sample. However, for many common analytes that would benefit from concentration (e.g., initial concentrations below 1 nM), where the capture moiety has an dissociation constant of similar or higher concentration (e.g., ≥1 nM), a capture region on the order of 0.1-15 mm long and 0.1-15 mm wide and 0.025-5 mm thick is used when processing samples on the order of 0.5-50 mL in approximately 1 hour or less.

Figure 5:
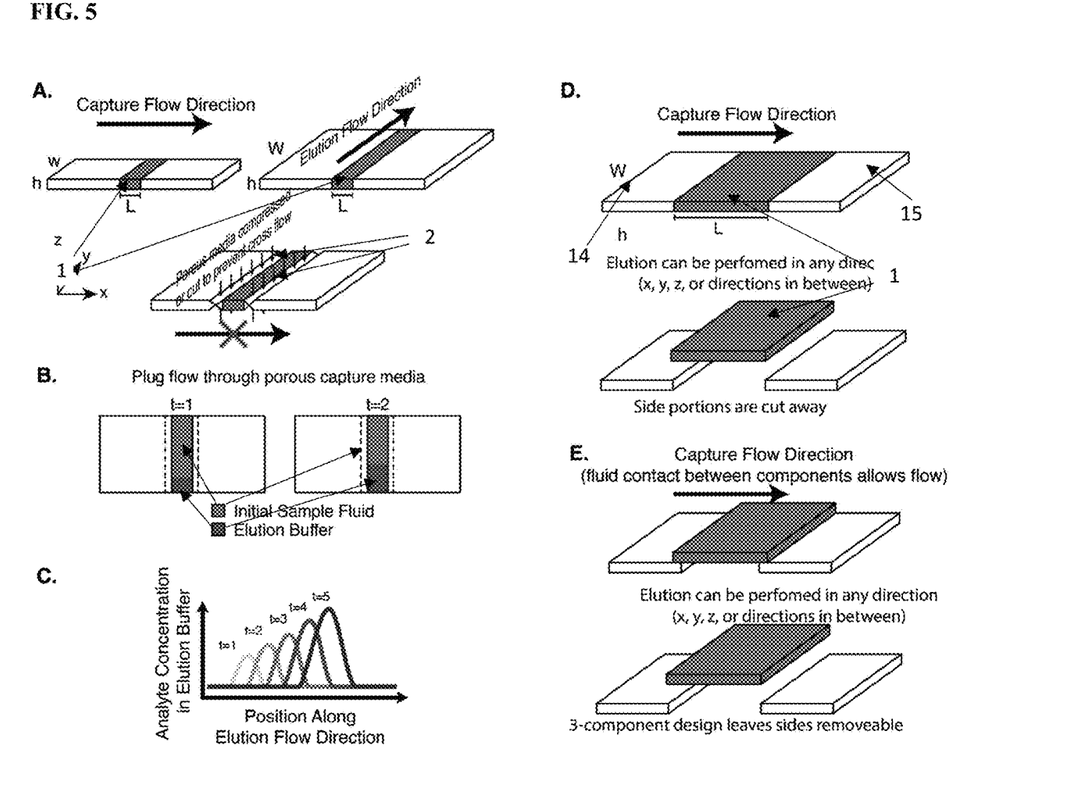

In some embodiments, the plug-like flow of fluid through porous material is leveraged to minimize elution volume while increasing cross sectional area of the capture region, thereby minimizing flow velocity while maximizing volumetric flow rate. In some embodiments, this is done by a combination of plug flow and eluting the analyte out of the capture region transversely to the direction of capture flow, as illustrated and described in FIG. 5. FIG. 5 shows an exemplary plug flow embodiment of the present disclosure. FIG. 5A (top panels) illustrates capture region 1 having length L. The direction of analyte capture (top left) is perpendicular to the direction of elution (top right). The bottom panel of FIG. 5A shows the use of compression or cut zones 2 to restrict fluid flow to the capture region 1. FIG. 5D shows the use of a three-component capture and elution system to leverage plug flow. FIG. 5D shows capture region 1 and input region 14 and output region 15. In some embodiments, capture region 1 is physically separated from input and output regions 14 and 15 by cutting a single piece of substrate at the boundary of the capture region. In some embodiments, the capture region 1 and input and output regions 14 and 15 are separate materials of the same or different compositions. In some embodiments, the input and output regions are removed after capture of sample and before elution.

During elution, the plug-like flow of fluid transversely through the capture region accumulates analyte at the flow-front of the elution buffer. Thus, a heightened concentration of analyte accumulates in a fraction of the volume of the capture region. Therefore, the cross-sectional area normal to the capture flow direction is increased without a concordant increase in elution volume. This is illustrated in FIG. 5B-D. As shown in FIGS. 5B and 5E, the flow front of fluid passing through porous media approximates plug flow (i.e., remains flat and normal to the direction of flow). Therefore, as fluid passes transversely through capture region in the direction of elution, the flow front accumulates analyte as it elutes off of the capture substrate. As shown in FIG. 5C, only the flow front with accumulated analyte need be removed from the capture region instead of the entire volume of the capture region. Elution can be performed in the direction of concentration (x-direction), perpendicular to the plane of the pad (z-direction), another option is to elute in the y-direction, or potentially directions in between. Thus, elution volume can be minimized while increasing cross-sectional area for capture to achieve overall improved performance.

To implement this approach, elution of the analyte off the capture substrate (e.g., dissociation of the captured analyte from capture beads) should be significantly faster than the time it takes for elution flow to traverse the capture region width, W. This is often the case for pH and salt-based elution strategies.

Transfer Efficiency

Figure 6:
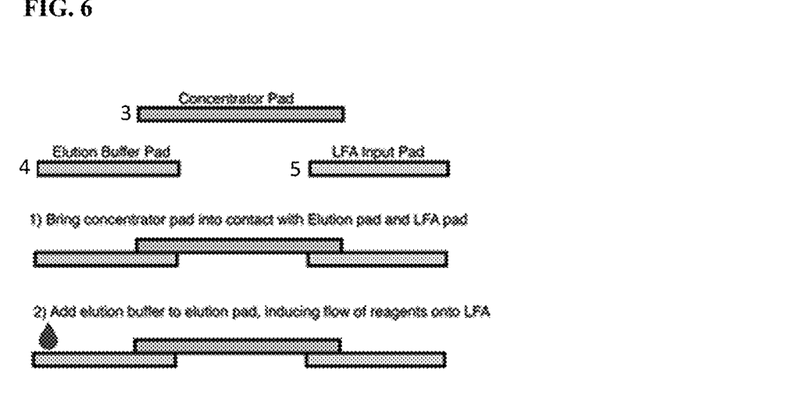
FIG. 6 shows an exemplary method to integrate substrate-based capture with lateral flow assays.

The mechanisms by which the sample concentration devices described herein interface with downstream detection (e.g., lateral flow assays) is often important to achieving a successful implementation of the sample concentration methods described herein for different applications. For example, in some embodiments, the substrate-based concentration compositions and methods described herein are used as a pre-concentration method for lateral flow assays (LFAs). In some embodiments, concentrated sample is eluted directly onto the LFA from a concentrator pad (FIG. 6). As shown in FIG. 6, the concentration pad 3 (e.g., comprising a plurality of capture regions) is brought into contact with the LFA input pad 5 and elution buffer pad 4 (middle panel of FIG. 6). Then, elution buffer is added to the upstream side of the concentration pad (e.g., via the an elution buffer pad) to flow elution buffer through the concentration pad (bottom panel of FIG. 6). The elution buffer causes release of the captured analyte. Fluid flow carries the eluate onto the LFA for detection. In some embodiments, an elution pad is not utilized. For example, in some embodiments (not shown in FIG. 6), the concentration pad 3 provides a location for dispensing elution buffer directly onto the concentration pad 3.

Figure 7:
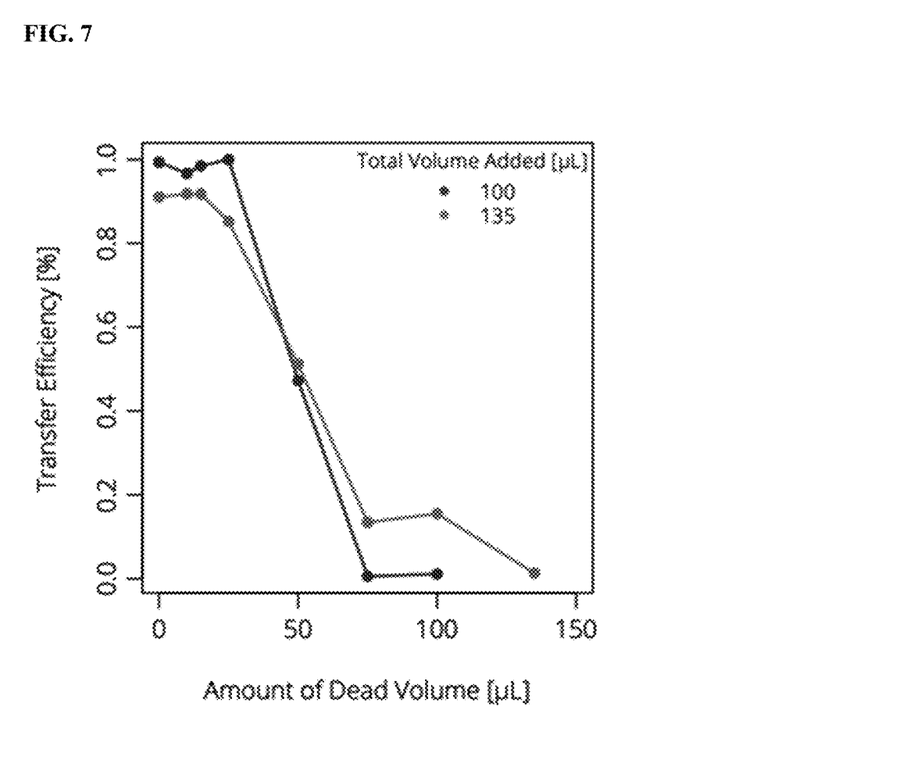
FIG. 7 shows that increasing dead-volume dramatically reduces LFA signal.

In some embodiments, the present disclosure provides compositions and methods that optimize sample transfer inefficiencies that arise from the presence of fluid in the concentrator pad prior to addition of elution buffer, e.g., 'dead volume'. The dead volume is largely devoid of target analyte. When elution buffer is introduced, the dead volume moves from the concentrator pad, downstream, onto the LFA in front of the elution buffer and, therefore, the eluted analyte. Given that LFA's typically allow <~50 µL of volume to flow past the test line for detection, if analyte is not in the first ~50 µL of fluid that is put onto the LFA, then the analyte is not detected (FIG. 7). In some embodiments, the flow through the absorbent materials is approximated by plug-flow, creating a first-in-first-out flow scheme. However, tortuous flow and diffusion cause the boundary between the two fluids (dead volume and elution buffer) to mix. Therefore, the boundary between dead volume and elution buffer blurs slightly. However, in practice, when dead volume is <~30 µL, maximal detection signal is obtained. However, when dead volume >~50-75 µL signal can drop to below 10%. In some embodiments, dead volume is reduced by diverting the first portion of flow to absorbent pads, and allowing subsequent flow to continue onto the LFA, for example as described in FIG. 8.

Figure 8:
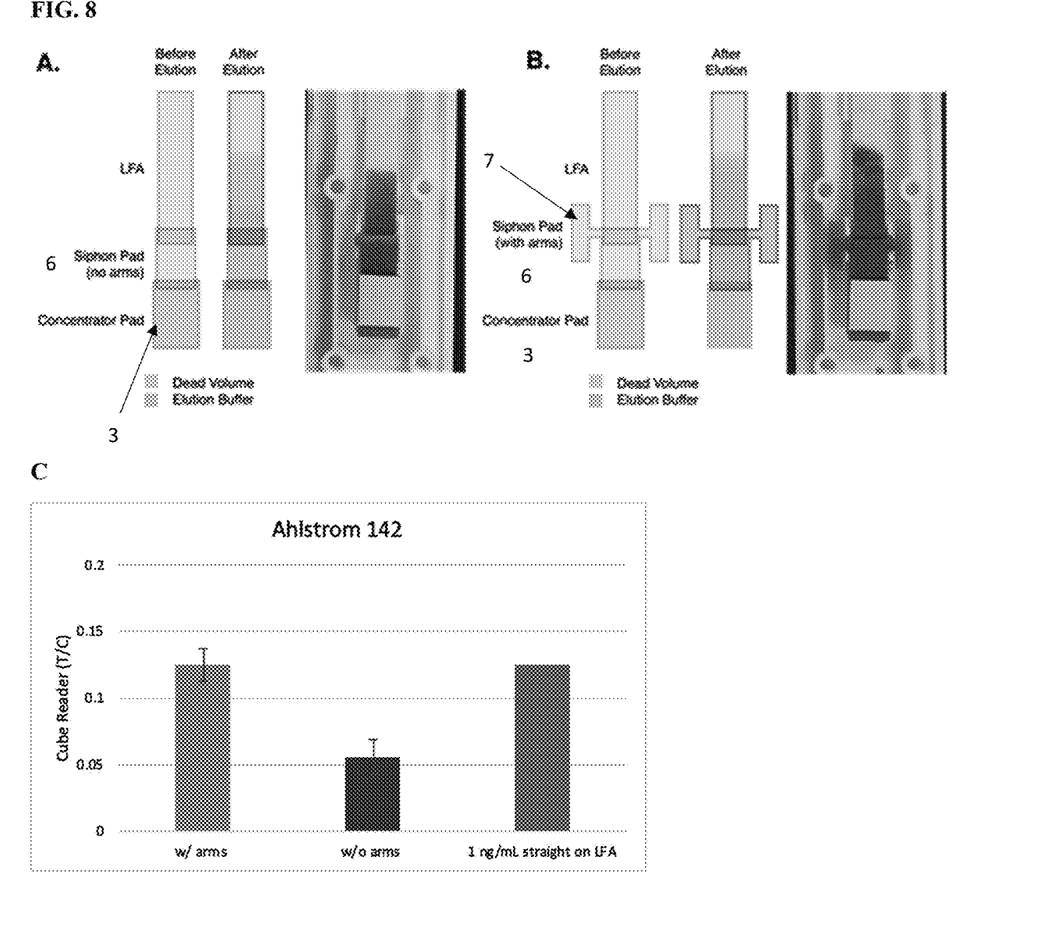
FIG. 8 shows an exemplary siphon component to eliminate dead volume. (A) Schematic and image of elution without siphon arms. Dead volume (red) proceeds downstream to LFA. (B) Schematic and image of siphon with arms that enable diversion of dead volume (red), allowing elution buffer (blue) to proceed first onto the LFA. (C) Siphon arms completely rescue signal lost due to dead-volume.

As shown in FIG. 8, embodiments of the present disclosure provide a siphon component 6 for diverting the initial flow. In some embodiments, the siphon 6 has side features referred to here as 'arms' 7 that create a place to divert fluid into prior to allowing fluid comprising analyte to proceed onto the LFA. This is illustrated in FIG. 8. In FIG. 8A, a siphon 6 without arms is placed in operable communication with concentrator pad 3 comprising concentrated sample. After addition of elution buffer, the dead volume lacking sample flows onto the LFA (top shaded area of FIG. 8A). In contrast, in FIG. 8B, a siphon 6 with arms 7 is utilized. In this case, the dead volume flows into the arms 7, allowing only concentrated sample comprising analyte to flow onto the LFA. FIG. 8C shows a graph of signal loss with and without the use of a siphon with arms.

The sizes of the siphon arms are directly related to the amount of fluid that is diverted. When the siphon is made of an absorbent material with sufficiently strong capillary wetting, the fluid completely wets the siphon pad before continuing on to the input pad of the LFA. Therefore, not all materials are appropriate for use with each concentrator pad and LFA. For example, when highly porous materials with weaker wetting properties were used, it was found that the fluid wets along the bottom surface of the siphon first, then "fill" the siphon from bottom to top. Better performing materials wet from upstream to downstream as with plug-like flow. When bottom-to-top filling occurs, the first-in-first-out plug-flow scheme is broken and flow diversion is inefficient. Therefore, optimal siphon design uses smaller pore size materials with good wettability for the particular reagents being used to maintain plug-like flow and saturation prior to passing fluid onto the input pad of the LFA. It is also important to note that diverting too much volume will eventually divert elution buffer containing analyte. Therefore, there is an optimal balance to the degree of siphoning that is readily determined via experiments with different siphon arm sizes. For typical LFAs and capture pad geometries, this is on the order of ~60 µL.

Some materials, such as cellulose fiber, cotton fiber or cotton/glass blend fiber pads (e.g., commercially available Ahlstrom-Munksjö grade 142 and Millipore CFSP223000 material), provide excellent wetting properties to support first-in-first-out plug-flow for aqueous sample and elution fluids. However, some materials are more appropriate than others. For example, it was observed that the 142 material performs better with low pH elution compared to the CFSP223000 given that the cellulose material is more susceptible to acid degradation which can affect downstream assays such as LFAs. Thus, siphon materials can be optimized for different sample types and elution strategies.

Elution Efficiency

Once captured, target analyte can be difficult to elute off the substrate. Thus, ideally, the chosen capture chemistry should provide a very high value for $k_{on}$ yet allow the target to be eluted off rapidly and efficiently. The ease of elution can be linked to $k_{off}$ but is not always directly correlated. Therefore, in some embodiments, $k_{on}$ is maximized and $k_{off}$ is minimized while keeping in mind efficient and rapid elution and recognizing that improvements in $k_{on}$ are significantly more important than $k_{off}$ in terms of capture efficiency.

Figure 9:
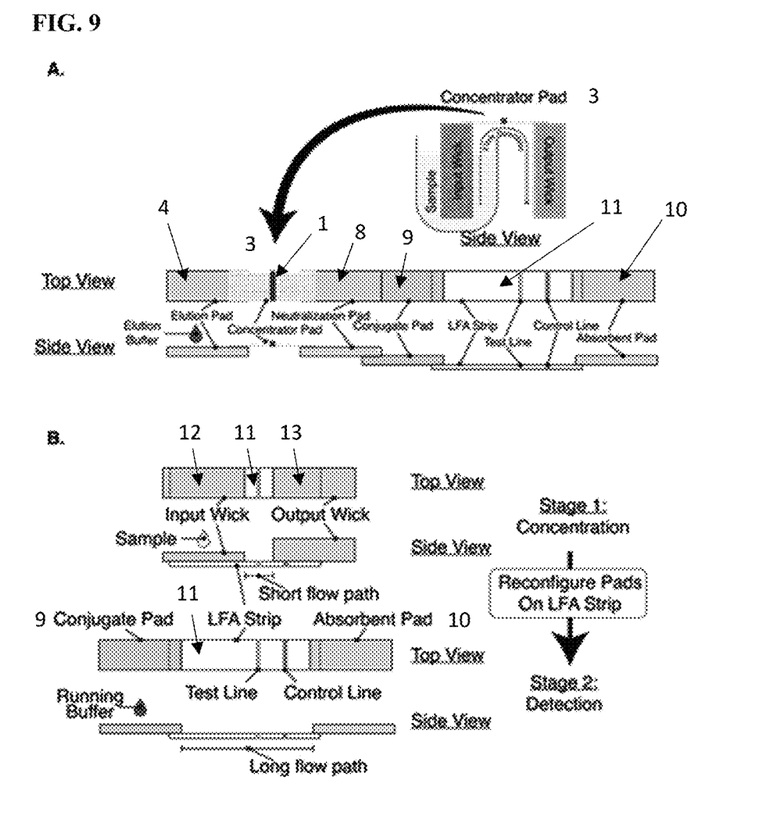
FIG. 9 shows exemplary substrate-based concentration configurations. (A) Embodiment using a large pore absorbent material laden with capture beads to concentrate analyte from a sample. (B) Embodiment that utilizes concentration directly on a nitrocellulose membrane of the LFA strip.

For example, in some embodiments, given the understanding provided by the above optimizations to Eq 2, an alternative approach to sample concentration that eliminates the need for both elution and transfer is utilized (FIG. 9). This approach builds upon traditional lateral flow assay (LFA) methodology. In an LFA, it is common to use a microporous nitrocellulose (NC) membrane as the primary component. On the NC membrane, approximately 0.5 µg of antibody (Ab) is deposited in a line approximately 1 mm wide across the full width (~5 mm) of the ~20 mm long NC strip. The NC is typically around ~160 µm thick. Therefore, antibody is constrained to a region 0.16 mm×1 mm×5 mm (or 0.8 This line will be referred to as the 'test line'. However, the present disclosure is not limited to a test line. In some embodiments, the test region is a line, spot, or other configuration. Upstream of the test line is a pad that contains Ab-functionalized nanoparticles (beads) that mix with incoming fluid, resulting in binding of the analyte to the beads if analyte is present. If the beads have analyte bound, they become bound to the test line, where if no analyte is on the beads, the beads continue downstream to another line of antibody specific to the antibody on the beads, called the control line. The control line binds beads missed by the test line. Downstream of the test line is an absorbent pad that continues to wick away fluid from the NC membrane to maintain flow.

Integration of substrate-based sample concentration with existing LFA technology is illustrated in FIG. 9A. Sample in capture region 1 of concentrator pad 3 is placed in operable communication with elution pad 4, optional neutralization pad 8, and conjugate pad 9, which is in operable communication with LFA 11 and optional absorbent pad 10. Elution buffer is added to elution pad 4. The buffer flows from the elution pad to concentrator pad 3, driving the concentrated sample into the LFA strip for detection.

In the alternate embodiment shown in FIG. 9B, a multi-step procedure is used to alter the sequence of LFA operation to enable pre-concentration directly on the LFA as a way to (i) improve performance of sample concentration, (ii) seamlessly integrate pre-concentration and detection while eliminating the need for transfer, and (iii) eliminate the elution and rebinding steps, without the need to perform any elution and re-capture of the analyte. Beads are eliminated by changing the capture material to a nitrocellulose (NC) membrane that is similar to that used in lateral flow assays. Antibody is immobilized non-specifically to the nitrocellulose (NC) membrane to enable capture as fluid flows through the porous material. This is commonly done in lateral flow assays and is advantageous because it does not require functionalization chemistry. However, alternative methods for directly or indirectly immobilizing the capture antibody can be used (e.g., biotin-avidin chemistry or covalent linking to the substrate).

As illustrated in FIG. 9B, a multi-step procedure is utilized to concentrate and detect using the LFA. In the first step (upper portion of FIG. 9B), an LFA test strip 11 comprising an analyte specific antibody immobilized to the test line is placed in operable communication with an input wick 12 and an output wick 13 (e.g., both comprising an absorbent material). The immobilized antibody binds to analyte in the sample and concentrates analyte in the LFA. Optionally, washing or other treatment procedures are then performed by placing the input wick in communication with alternative reagents. The input and output wicks are then removed and the LFA strip 11 comprising concentrated analyte is placed in operable communication with a conjugate pad 9 comprising nanoparticles conjugated to a secondary detection antibody and absorbent pad 10. Running buffer is added and detection proceeds as in a standard LFA.

This approach optimizes Eq 2 in multiple ways. Elution efficiency and transfer efficiency become 100% given that no elution or transfer steps are needed. Also, capture efficiency is enhanced in multiple ways. Antibody concentration during capture is enhanced. Instead of 3.5 µg of Ab in a 60 µL capture region (i.e., 58 µg/mL), 0.5 µg of Ab is put into a capture region of 0.8 (625 µg/mL), providing a ~10× gain in capture Ab concentration. In addition, it is possible to use an antibody with the best binding characteristics alone. In some embodiments, this translates to a 10× improvement in both $k_{on}$ and $k_{off}$. Combined with the 10× increase in capture Ab concentration, this results in a 10,000× fold gain in the capture parameter a (Eq 3, 10×10^2/0.1=10,000). Therefore, this alternative approach provides dramatic improvements in the ability to concentrate from concentrations of analyte as much as 1000× lower than existing technologies.

The primary challenge of working with an NC membrane is that the resistance to flow is dramatically higher than the porous material used to entrap beads in other approaches. The approach described in FIG. 9B addresses this by creating a very short flow path through the NC membrane for the concentration step, yet uses a longer flow path more suitable for subsequent binding of nanoparticles at the test line. Thus, unlike typical LFA sequencing, where analyte interacts first with nanoparticles and then the test line; this embodiment interacts the analyte with the test line first, then the nanoparticles interact with analyte already bound at the test line. This sequencing is often less optimal (~10%). Therefore, for many applications the potential gain in sensitivity is closer to ~100× with this approach.

In some embodiments, different stages of reagent flow are used to address inefficiencies in elution and detection. In some embodiments, the analyte is allowed to flow over the test region (e.g., line) of an LFA first, followed by flow of nanoparticles for detection. This differs from a more traditional method of operating an LFA, where analyte and detection particles are allowed to flow simultaneously down the LFA. Employing such a two-stage approach allows one to eliminate the need for delicate timing of component release and elimination of dead volume that may separate the detection particles from the analyte. One way to accomplish this is to remove the conjugate pad containing the detection particles from a traditional LFA. Elute captured analyte onto the LFA, then bring the unused conjugate pad into contact with the LFA membrane and flow additional fluid to carry the detection particles over the test region.

Alternatively, another approach to eliminating inefficiency in transfer and elution is to leverage simultaneous elution of the capture molecule/mechanism and the analyte from the capture substrate. For example, in some embodiments, this is accomplished using an IgG antibody immobilized on a capture bead using protein G. The use of protein G allows the analyte to be more efficiently eluted from the bead because the high-affinity interaction between the antibody and analyte can be difficult to dissociate whereas the antibody protein G interaction is more easily dissociated. For example, the interaction between A194 anti-LAM antibody and LAM is sufficiently strong to resist elution with pH2 elution buffer whereas IgG and protein G is not. Additionally, with the use of protein G, both the antibody and analyte are co-eluted from the bead. Upon neutralization downstream, the analytes can rebind. Or, for example, with the use of A194 anti-LAM antibody, the antibody and analyte stay bound together throughout the process of elution and neutralization. In the case where an LFA is used for detecting the eluted components, this strategy provides improved detection efficiency compared to attempting to recapture eluted analyte onto a functionalized detection particle (e.g., gold nanoparticles or cellulose nanobeads). This is because a detection particle limits the (i) diffusion, (ii) conformation, (iii) availability of the capture site on the antibody and also (iv) often does not allow for efficient immobilization of capture moiety to the particle (e.g., non-specific adsorption of antibody specific to the analyte). Furthermore, unlike the case where only analyte is eluted, the capture molecule flows along with the analyte downstream regardless of any potential dead volume in the system. When co-eluting the capture moiety and analyte and detecting on an LFA, detection (e.g., via nanoparticles functionalized with antibody) is performed after the antibody-analyte complex is bound at the test region (e.g., via anti-rabbit antibody). In some embodiments, the biotinylated antibody is modified to provide higher affinity capture at the test region, such as via biotinylation of the antibody. In such embodiments, where detection occurs after binding to the test line, dead-volume is also not a concern, as sufficient volume is flowed through the system to allow both analyte and detection particles to pass over/interact with the test region.

Figure 12:
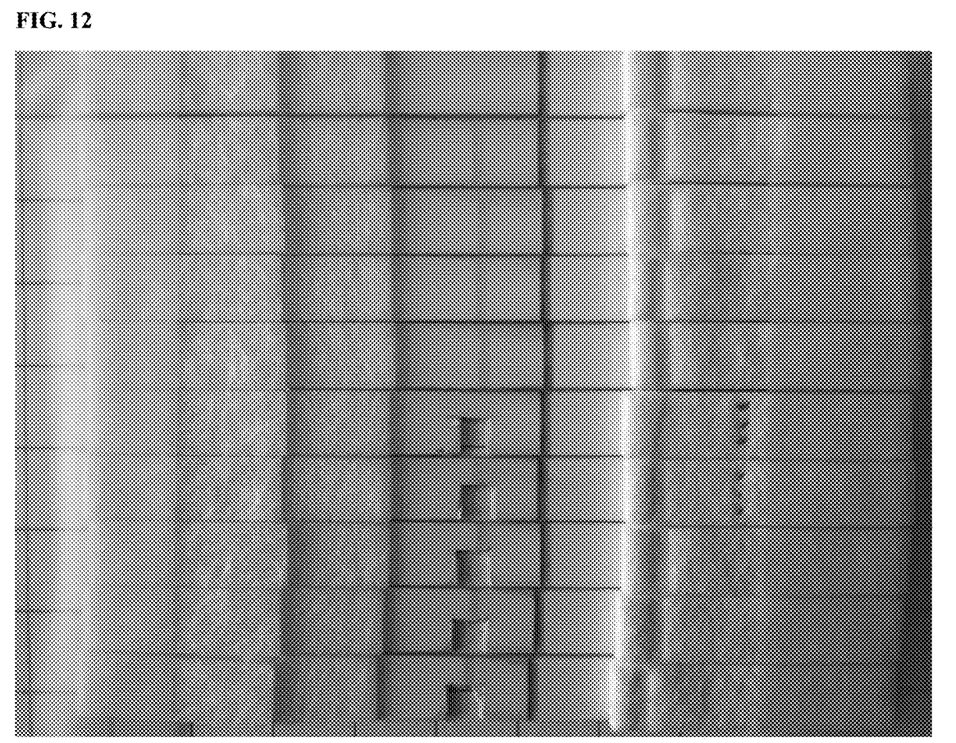
FIG. 12 shows an image of an LFA with reduced width at the test line.
Figure 13:
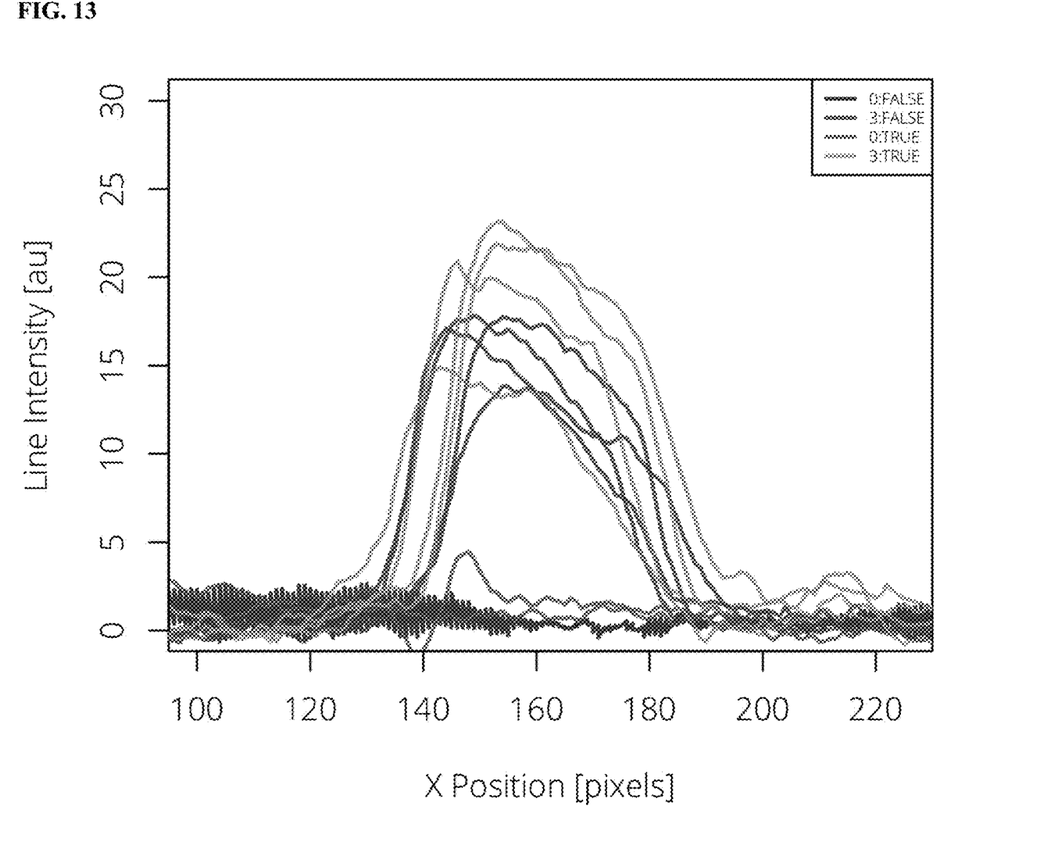
FIG. 13 shows a graph of intensity of test line of an LFA with reduced width at the test line. The x-axis represents the position along the LFA at which the intensity is measured (i.e., an intensity profile). In the legend, a 0 or 3 is used to indicate whether 0 ng/mL or 3 ng/mL of LAM was applied to the LFA. In the legend, TRUE and FALSE are used to indicate whether the LFA had the width of the test line reduced by 50% (TRUE=50% width, FALSE=100% width).

In some embodiments, LFAs are altered to increase signal intensity. For example, in some embodiments, the width of the LFA is reduced at the test line relative to its other regions. Experiments were conducted that compared the intensity of the readout between LFAs that were unaltered to those that with a reduced width at the test line. Results are shown in FIGS. 12 and 13. FIG. 12 shows images of altered LFAs. Devices 5 and 10 are negative controls while the others received 3 ng/mL of lipoarabinomannan (LAM). FIG. 13 shows a graph of intensity of test line of an LFA (y-axis) with reduced width at the test line. The x-axis represents the position along the LFA at which the intensity is measured (i.e., an intensity profile). In the legend, a 0 or 3 is used to indicate whether 0 ng/mL or 3 ng/mL of LAM was applied to the LFA. In the legend, TRUE and FALSE are used to indicate whether the LFA had the width of the test line reduced by 50% (TRUE=50% width, FALSE=100% width). The increased intensities are observed when using a reduced width test line.

Reducing the width of the LFA at the test region (e.g., line) forces all the reagents/analyte to pass over a smaller portion of the test region, causing a darker signal to accumulate (n=4, m=4, p=0.03). This produced a 25% increase in line intensity, which using a visual score card changes from a reading of 4 to a reading of 5. A single point increase on the visual scale is associated with roughly a 2× increase in analyte concentration on the test line, which is commensurate with the 50% reduction in test line width. Such alterations are particularly useful in embodiments where a visual readout is required (e.g., most at home tests and low-resource applications such as tuberculosis testing). The LFA is narrowed only in the region close to the test line to avoid unnecessary increase in LFA flow resistance (e.g., test time). Although the image shown in FIG. 12 is cut manually, in some embodiments, die-cutting is used or the material is initially fabricated with a narrower region.

As exemplified in FIG. 12, in some embodiments, the present disclosure provides an LFA comprising a sample detection membrane comprising an upstream zone, a test line zone, and a control zone, wherein the test line zone has a width at least 25% (e.g., at least 25%, 35%, 45%, 50%, 55%, 60%, or 70%) less that the upstream zone and the downstream zone. In some embodiments, the region removed is at least as wide as the test line (e.g., 1×, 1.5×, 2×, 2.5×, 3×, or more in width).

In some embodiments, sample concentration and/or device operation are automated or robotically controlled. For example, in some embodiments, operation is performed autonomously or semi-autonomously.

The assay systems described herein find use in a variety of immunoassay applications. Examples include, but are not limited to, hormones (e.g., pregnancy or ovulation hormones), infectious disease markers or markers for environmental monitoring.

In some embodiments, the analyte to be detected is a protein, peptide, carbohydrate, lipid, small molecule, antibody, nucleic acid, virus, lipid, glycolipids, virus particle, drug, drug metabolite or small molecule. Specific examples include, but are not limited to, human chorionic gonadotrophin, luteinizing hormone, estrone-3-glucoronide, pregnanedio13-glucoronide, insulin, glucagon, relaxin, thyrotropin, somatotropin, gonadotropin, follicle-stimulating hormone, gastrin, bradykinin, vasopressin, polysaccharides, lipoarabinomannan, estrone, estradiol, cortisol, testosterone, progesterone, chenodeoxycholic acid, digoxin, cholic acid, digitoxin, deoxycholic acid, lithocholic acids; vitamins, thyroxine, triiodothyronine, histamine, serotonin, prostaglandin, drugs, drug metabolites, ferritin or CEA.

In some embodiments, immunoassays utilize antibodies to a purified protein (e.g., analyte). Such antibodies may be polyclonal or monoclonal, chimeric, humanized, single chain or Fab fragments, which may be labeled or unlabeled, all of which may be produced by using well known procedures and standard laboratory practices. See, e.g., Burns, ed., *Immunochemical Protocols*, 3$^{rd}$ ed., Humana Press (2005); Harlow and Lane, *Antibodies: A Laboratory Manual*, Cold Spring Harbor Laboratory (1988); Kozbor et al., *Immunology Today* 4: 72 (1983); Köhler and Milstein, *Nature* 256: 495 (1975). In some embodiments, commercially available antibodies are utilized.

The devices and methods of the present disclosure are suitable for use with a variety of sample types. Exemplary sample types include, but are not limited to, blood, serum, nasal fluid, urine, sweat, plasma, semen, cerebrospinal fluid, tears, pus, amniotic fluid, saliva, lung aspirate, gastrointestinal contents, vaginal discharge, urethral discharge, chorionic villi specimens, skin epithelials, genitalia epithelials, gum epithelials, throat epithelials, hair or sputum.

In some embodiments, kits, systems and/or devices of the present invention are shipped containing all components necessary, sufficient or useful to perform substrate-based sample capture and/or concentration and/or immunoassays. In other embodiments, additional reaction components are supplied in separate vessels packaged together into a kit. Kits may further comprise appropriate controls and/or detection or indicator reagents.

The foregoing description of illustrative embodiments of the disclosure has been presented for purposes of illustration and of description. It is not intended to be exhaustive or to limit the disclosure to the precise form disclosed, and modifications and variations are possible in light of the above teachings or may be acquired from practice of the disclosure. The embodiments were chosen and described in order to explain the principles of the disclosure and as practical applications of the disclosure to enable one skilled in the art to utilize the disclosure in various embodiments and with various modifications as suited to the particular use contemplated. It is intended that the scope of the disclosure be defined by the claims appended hereto and their equivalents.

What is claimed is:

1. A system, comprising:
   a) a sample concentration device comprising a substrate comprising a plurality of wicking regions and a plurality of capture regions, wherein each of said capture regions comprises a plurality of analyte specific capture reagents, wherein each of said capture regions comprises two fluid isolation zones on either side of said capture region, wherein said fluid isolation zones are physically separatable from said capture region;
   b) a detection membrane that receives concentrated sample from a capture region via a primary flow path; and
   c) a siphon pad in operable communication with said sample concentration device and said detection membrane, wherein said siphon pad that comprises one or more arms that direct flow from said sample concentration device down a path different than the primary flow path, and wherein the siphon pad does not comprise analyte specific capture reagents.

2. The system of claim 1, wherein said fluid isolation zones comprise a compressed or cut region of said substrate.

3. The system of claim 2, wherein said fluid isolation zones physically separate said capture region from said wicking regions.

4. The system of claim 1, wherein said substrate comprises a porous material.

5. The system of claim 1, wherein said sample concentration device comprises at least 2 parallel capture regions.

6. The system of claim 5, wherein said capture regions are spaced at a width of approximately 1.3 times a depth of said substrate.

7. The system of claim 1, wherein said sample concentration device comprises at least 3 parallel capture regions.

8. The system of claim 1, wherein said sample concentration device comprises at least 6 parallel capture regions.

9. The system of claim 1, wherein said capture regions have a width approximately equal to a depth of said substrate.

10. The system of claim 1, wherein said analyte specific capture reagent comprises particles comprising an analyte specific binding molecule selected from the group consisting of antibody, a lectin, a carbohydrate, a dye, biotin, and streptavidin.

11. The system of claim 1, wherein said wicking regions comprise an input wick and/or an output wick in fluid communication with said sample capture regions.

12. The system of claim 1, wherein each of said capture regions is 0.1-15 mm long, 0.1-15 mm wide and 0.025-5 mm thick.

13. The system of claim 1, wherein said analyte specific capture reagents are applied via spraying.

14. The system of claim 1, wherein said wicking regions and said capture region are physically separate components.

15. The system of claim 1, said siphon pad comprises a porous substrate.

16. The system of claim 15, wherein said porous substrate comprises cellulose fiber, cotton fiber, or fiber comprising glass and cotton.

17. The system of claim 1, wherein said siphon pad is configured to hold up to 100 μl of fluid.

18. The system of claim 1, wherein said siphon pad comprises a pore size and/or wettability such that fluid introduced into said device is absorbed by said siphon pad prior to flowing downstream.

19. The system of claim 1, wherein said detection membrane is a component of a lateral flow assay device.

20. The system of claim 1, wherein said fluid isolation zones are oriented perpendicular to a direction of capture flow.

21. The system of claim 1, wherein said system further comprises an elution component in operable communication with said sample concentration device.

22. A method of concentrating an analyte, comprising:
   a) contacting a sample comprising said analyte with the sample concentration device of the system of claim 1 such that said analyte binds to said capture regions; and
   b) eluting said analyte from said capture regions.

* * * * *

UNITED STATES PATENT AND TRADEMARK OFFICE
CERTIFICATE OF CORRECTION

| | |
|---|---|
| PATENT NO. | : 12,247,976 B2 |
| APPLICATION NO. | : 17/313715 |
| DATED | : March 11, 2025 |
| INVENTOR(S) | : Jay Warrick and David Beebe |

It is certified that error appears in the above-identified patent and that said Letters Patent is hereby corrected as shown below:

In the Claims

Claim 1, Column 19, Line 23:
"brane, wherein said siphon pad that comprises one or".

Whereas it should read:
"brane, wherein said siphon pad comprises one or".

Page 1 of 1

Signed and Sealed this
Twenty-ninth Day of April, 2025

Coke Morgan Stewart
*Acting Director of the United States Patent and Trademark Office*